United States Patent
Brengle et al.

(10) Patent No.: US 6,428,518 B1
(45) Date of Patent: Aug. 6, 2002

(54) MEDICATION DELIVERY CONTAINER

(75) Inventors: David R. Brengle, San Diego, CA (US); Michael W. Kleeman, Sudbury, MA (US); Jeremy David Fennelly, Escondido; Douglas Everett Merritt, Oceanside, both of CA (US); Ronald Jay Forni, Littleton, MA (US)

(73) Assignee: Tandem Medical, San Diego, CA (US)

( * ) Notice: Subject to any disclaimer, the term of this patent is extended or adjusted under 35 U.S.C. 154(b) by 0 days.

(21) Appl. No.: 09/434,975

(22) Filed: Nov. 5, 1999

(51) Int. Cl.[7] .............................................. A61M 5/00
(52) U.S. Cl. ..................................................... 604/191
(58) Field of Search .............................. 604/80, 83, 81, 604/82, 84, 85, 410, 408, 411, 415, 191; 206/219, 221, 438

(56) References Cited

U.S. PATENT DOCUMENTS

| | | | | |
|---|---|---|---|---|
| 2,254,994 A | * | 9/1941 | Butland ........................ 604/80 |
| 3,469,578 A | | 9/1969 | Bierman ....................... 128/214 |
| 3,543,966 A | | 12/1970 | Ryan et al. .................... 222/94 |
| 3,941,126 A | * | 3/1976 | Dietrich et al. ................. 604/80 |
| 4,507,114 A | | 3/1985 | Bohman et al. .............. 604/111 |
| 4,512,764 A | | 4/1985 | Wunsch ........................ 604/80 |
| 4,522,622 A | | 6/1985 | Peery et al. .................. 604/191 |
| 4,548,606 A | * | 10/1985 | Larkin .......................... 604/414 |
| 4,559,036 A | | 12/1985 | Wunsch ........................ 604/81 |
| 4,576,603 A | | 3/1986 | Moss ........................... 604/410 |
| 4,741,736 A | | 5/1988 | Brown ......................... 604/134 |
| 4,753,371 A | | 6/1988 | Michielin et al. ........... 222/144.5 |
| 4,784,157 A | | 11/1988 | Halls et al. .................. 128/762 |
| 4,823,833 A | | 4/1989 | Hogan et al. ................ 137/567 |
| 4,957,436 A | | 9/1990 | Ryder ........................... 433/88 |
| 4,997,083 A | | 3/1991 | Loretti et al. ................. 206/219 |
| 5,176,634 A | | 1/1993 | Smith et al. ................... 604/87 |
| 5,286,262 A | * | 2/1994 | Herweck et al. ............... 604/80 |
| 5,308,334 A | | 5/1994 | Sancoff et al. ............... 604/131 |
| 5,318,515 A | | 6/1994 | Wilk ............................. 604/30 |
| 5,368,570 A | | 11/1994 | Thompson et al. .......... 604/131 |
| 5,394,907 A | | 3/1995 | Hjertman et al. ............... 141/1 |
| 5,431,496 A | | 7/1995 | Balteau et al. ................. 383/38 |
| 5,505,708 A | | 4/1996 | Atkinson ..................... 604/140 |
| 5,509,898 A | | 4/1996 | Isono et al. .................... 604/87 |
| 5,560,518 A | | 10/1996 | Cattrall et al. ................. 222/99 |
| 5,578,005 A | | 11/1996 | Sancoff et al. ................ 604/82 |
| 5,643,205 A | * | 7/1997 | Utterberg ....................... 604/80 |
| 5,658,271 A | * | 8/1997 | Loubser ....................... 604/410 |
| 5,853,388 A | | 12/1998 | Semel .......................... 604/82 |

OTHER PUBLICATIONS

I–Flow VIVUS 50 and VIVUS 100, Data Sheets, 5 pages, Jun. 1993.

* cited by examiner

*Primary Examiner*—Manuel Mendez
(74) *Attorney, Agent, or Firm*—Foley & Lardner; Stephen E. Reiter

(57) ABSTRACT

In accordance with the present invention, there is provided a medication delivery container that is preconfigured to administer an infusion therapy upon activation by a pump mechanism. The configuration of the bag can determine the sequence and amount of medication to be delivered. In one embodiment of the invention, the medication delivery container includes a multi-chamber bag, a manifold assembly and an administration set. The manifold assembly is configured with internal conduits and valves to direct output from each chamber of the bag to an output port in the manifold, and into the administration set. In additional embodiments, there are provided structures in the container to alleviate pressure drop during the application of pressure to the container. Invention containers provide improved infusion therapy administration which is particularly advantageous for reducing errors, infections and other complications associated with manual infusion techniques.

34 Claims, 9 Drawing Sheets

US 6,428,518 B1

MEDICATION DELIVERY CONTAINER

FIELD OF THE INVENTION

The present invention generally relates to apparatus for the intravenous infusion of medication in accordance with a predetermined medical therapy. Medication delivery containers of the invention are useful for improving the ease of administration of a variety of therapeutic agents.

BACKGROUND OF THE INVENTION

Intravenous medications including antibiotics and the like may be administered intermittently over an extended period of time. Each administration of an intravenous therapy generally follows a predefined procedure that often includes a series of manual steps. Such manual steps may include saline flushes and generally terminate with the application of anti-clotting medication. The manual steps in the therapy procedures are a principle source of error, infection, and other complications that may arise during intermittent infusion therapy.

Accordingly, there is still a need in the art for a means to improve the administration of intermittent medication infusion therapy. The present invention satisfies this and other needs in the art.

BRIEF DESCRIPTION OF THE INVENTION

The present invention overcomes many of the problems in the art by providing a medication delivery container designed to interface with a pump apparatus. The container comprises a multi-chamber bag and a manifold assembly for administering an infusion therapy upon activation by the pump mechanism. The multi-chamber bag has a plurality of chambers that are configured to deliver a predetermined volume of each medication of an infusion therapy at a predetermined time, duration and interval. The medication delivery container may include an administration set for delivering the medications from the manifold assembly to an infusion site. The container provides improved infusion therapy administration over manual infusion techniques and reduces opportunities for error, infection or other complications.

Alternatively, the invention may be embodied in a fluid delivery container including a bag having at least one fluid chamber. The container also includes structures for minimizing pressure drop which may be associated with a chamber upon the application of pressure to the respective chamber, thereby allowing relatively unimpeded fluid flow from the respective chamber to an associated conduit during the entire period during which pressure is applied to the chamber.

Another embodiment of the invention is a fluid delivery container for the automated infusion of a plurality of pharmacological agents. The container includes a plurality of chambers and a manifold assembly. Each chamber is configured with a respective geometry for controlling the administration of the plurality of pharmacological agents. Each chamber has a configuration that controls the volume of each pharmacological agent administered and the regimen by which said pharmacological agent is administered. The manifold assembly has a plurality of valves for controlling the administration of the plurality of pharmacological agents to an infusion site.

Alternatively, the invention may be embodied in a delivery container to be filled with pharmacological fluids associated with a desired medical infusion therapy for treatment of a patient. The container may include a plurality of chambers for containing the pharmacological fluids, and a manifold assembly for dispensing the pharmacological fluids. The manifold assembly is configured, and each chamber is sized and configured, to implement the desired medical therapy when the fluids are automatically infused into the patient.

DETAILED DESCRIPTION OF THE INVENTION

Figure 1:
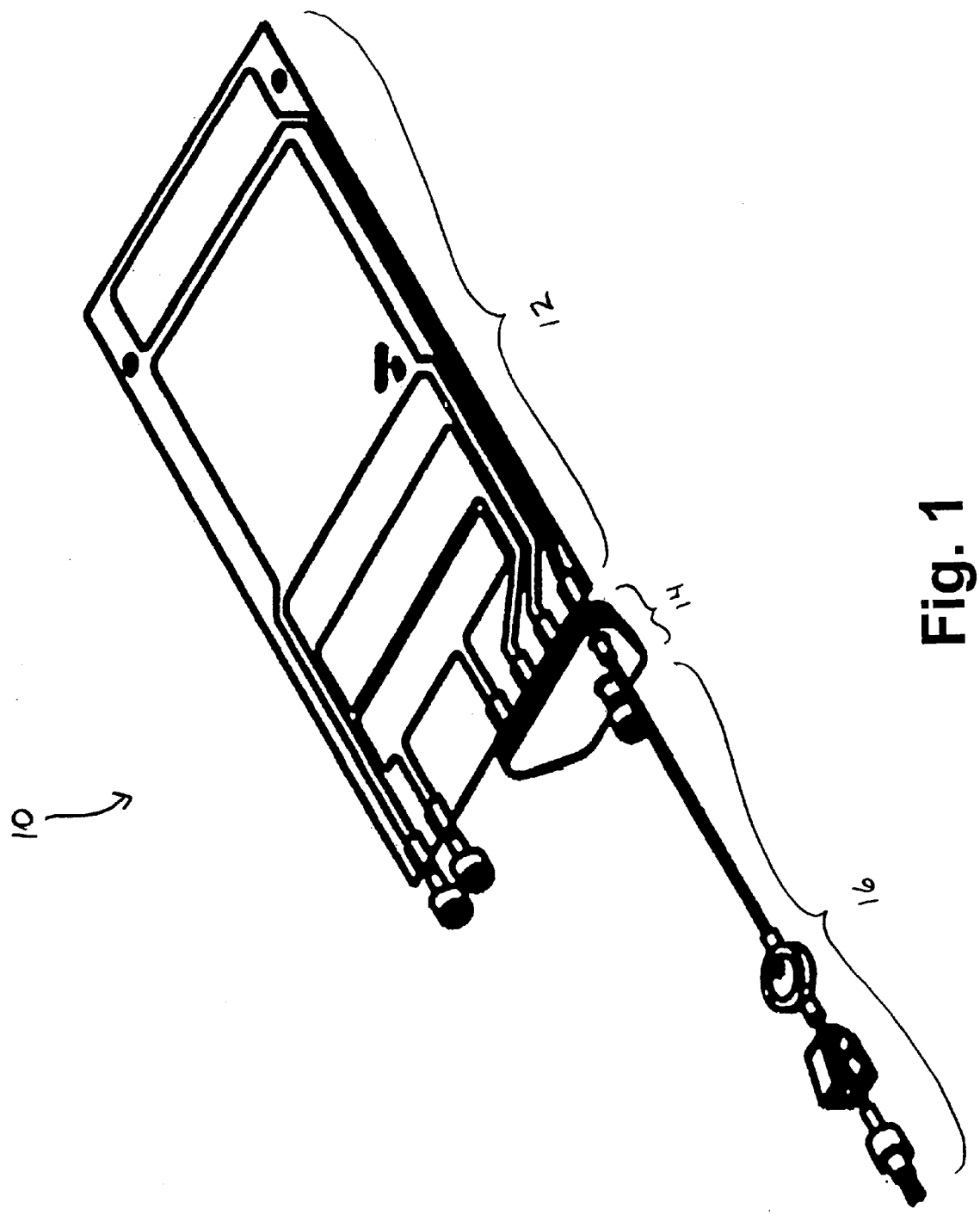
FIG. 1 is a perspective view of a medication delivery container according to the invention.

In accordance with the present invention, there is provided a medication delivery container that is configured to administer an infusion therapy upon activation by a pump mechanism. The container is preferably further configured to interface with a pump apparatus in a manner that securely maintains the container in position during pumping.

The invention container comprises a multi-chamber bag wherein the chambers are configured to deliver predetermined amounts of liquid medication at a predetermined rate and pressure. It is presently preferred that the container be formed of two sheets of flexible material. As will be appreciated by those of skill in the art, any suitable biocompatible flexible material may be employed in the construction of the bag, however, it is presently preferred that at least one side of the bag be transparent to facilitate viewing of the contents. For example, the flexible sheets may be ethyl vinyl acetate (EVA), polyvinyl chloride (PVC), polyolefin, or other suitable material. In one embodiment, the first sheet of flexible material has a relatively smooth inner surface and the second sheet of plastic has a texture, such as a taffeta texture, ribs, or the like, embossed on its inner surface. Alternatively, both sheets may have a patterned inner surface. The sheets are joined together around the perimeter of the container by any means suitable for forming an air and fluid-tight seal that can withstand the pressure generated by the pump apparatus. Fluid-tight seals are also formed between the individual chambers, and should have the same minimum pressure tolerances as the perimeter seals. Thus, the sheets are bonded together to create the patterns for the chambers, conduits, and ports. The materials may be bonded in a variety of ways, e.g., by a radio frequency (rf) seal, a sonication seal, a heat seal, adhesive, or the like, to form an air and fluid-tight seal as described herein.

Each chamber has one or more associated conduits. The conduits provide a pathway for fluid to enter and/or exit each chamber. The conduits can be integrally formed during construction of the container, for example, by leaving channels unbonded when the two sheets are fused together to form the container. Optionally, additional internal structure (e.g., rigid or semi-rigid tubing, or the like) may be provided to facilitate fluid flow to and from each chamber. It is presently preferred that the conduits through which medication exits the chambers lie outside of the compression region (i.e., the region to which pressure is directly applied by contact with a pressure applying structure in the pump apparatus). In this manner, mixing of residual medications in the conduits with subsequently administered medications from other chambers is minimized. Alternatively, the conduits may lie within the compression region, particularly if mixing is not a concern.

If the conduits are constructed by leaving unbonded channels in the container, the conduit will have a generally flat shape but enlarges to have a more tubular shape upon the application of pressure to the corresponding chamber. The shape of the conduit depends on the strength of the materials used to construct the bag and the pressure of the fluid therein. Specifically, more rigid or thicker materials are more difficult to flex thus requiring greater pressure for enlarging the conduit. Advantageously, the textured inner surface of at least one side of the container provides flow channels that allow liquid pressure to act along the length of the conduit to assist in opening the conduit upon the application of pressure to the respective chamber. Otherwise, if both inner sides of the container are smooth, surface tension may hold them together and a greater amount of pressure may be required to open the conduits and initiate flow.

In one embodiment of the present invention, the chambers and corresponding conduits from each chamber are arranged in the bag so that when pressure is applied sequentially from one end of the bag to the opposite end, individual chambers are sequentially activated. It is presently preferred that the pressure be applied evenly. Even, sequential application of pressure can be accomplished by employing a constant force spring, a roller attached to a constant force spring, a motor-driven roller, or the like.

It may be desirable to mix the contents of two or more chambers immediately prior to administration. Accordingly, in another embodiment of the present invention, frangible seals between two or more adjacent chambers may be formed. In this manner, upon application of pressure sufficient to rupture the seal, the contents of selected adjacent chambers will be mixed. The chambers may be side by side (i.e., configured so that pressure is applied to each substantially simultaneously), or in sequence.

Chambers may also be configured to have a "blow down" period between activation of one chamber and activation of the next chamber during an infusion sequence to prevent mixing of medications during the infusion. As described in greater detail below, this can be accomplished, for example, by providing a space between adjacent chambers, or the like.

It has been observed that there can be a pressure drop between a chamber and its corresponding conduit when pressure is applied to the contents of the bag. This is largely due to the formation of kinks in the bag when pressure is applied to the contents of the bag. The region of primary concern is the interface between the chamber and its corresponding conduit. Thus in one embodiment of the present invention, structure is provided to alleviate pressure drop between each chamber and its corresponding conduit. This can be achieved by one or more of several methods, including quilting of the chamber, incorporation into the chamber of internal structures (e.g., a stent, tubing, conduit bead(s), solid filament, or the like), or employing external structures (e.g., a source of pressure on the container, such as a protruding member of the pump apparatus, or the like), and the like.

Figure 2:
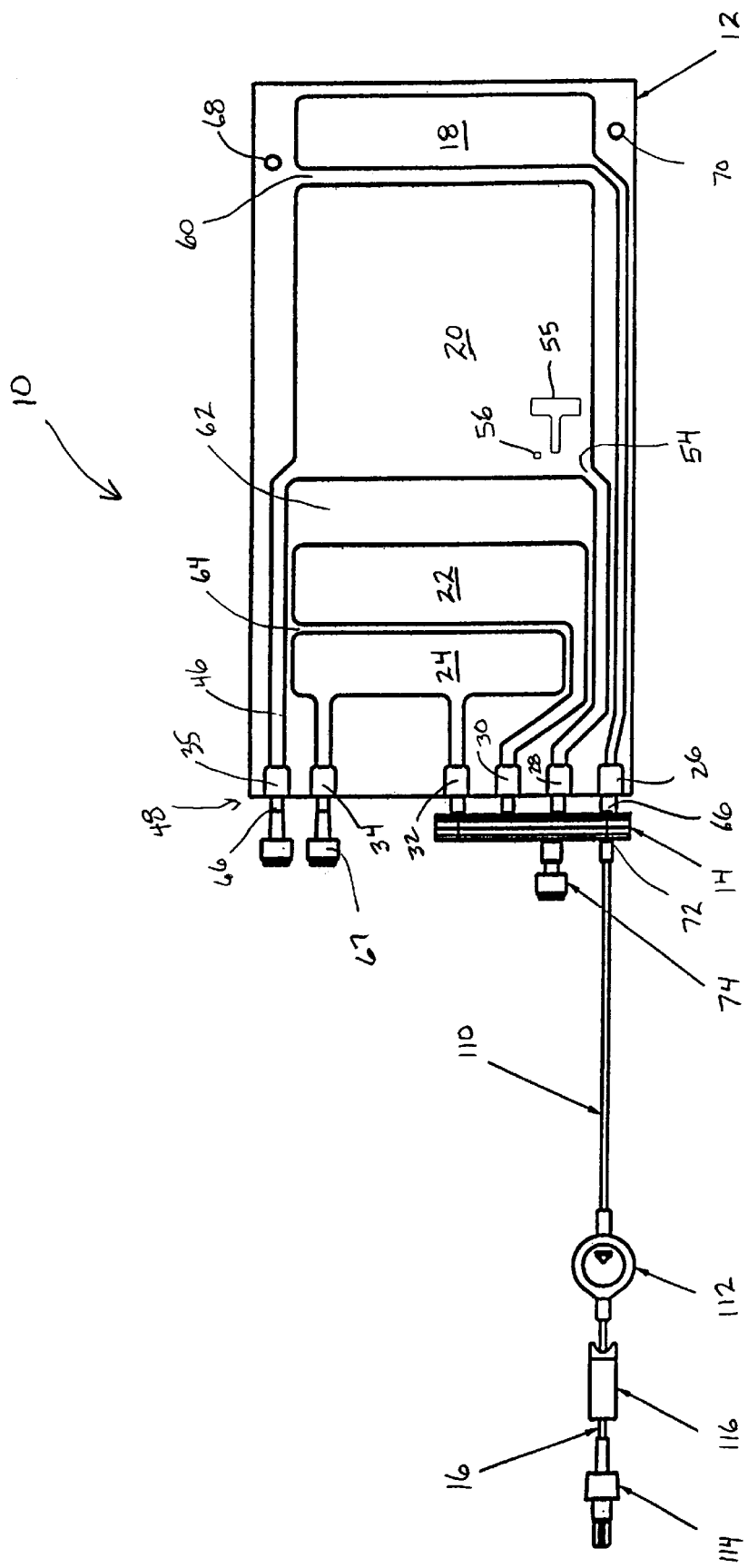
FIG. 2 is a plan view of the medication delivery container of FIG. 1.
Figure 5:
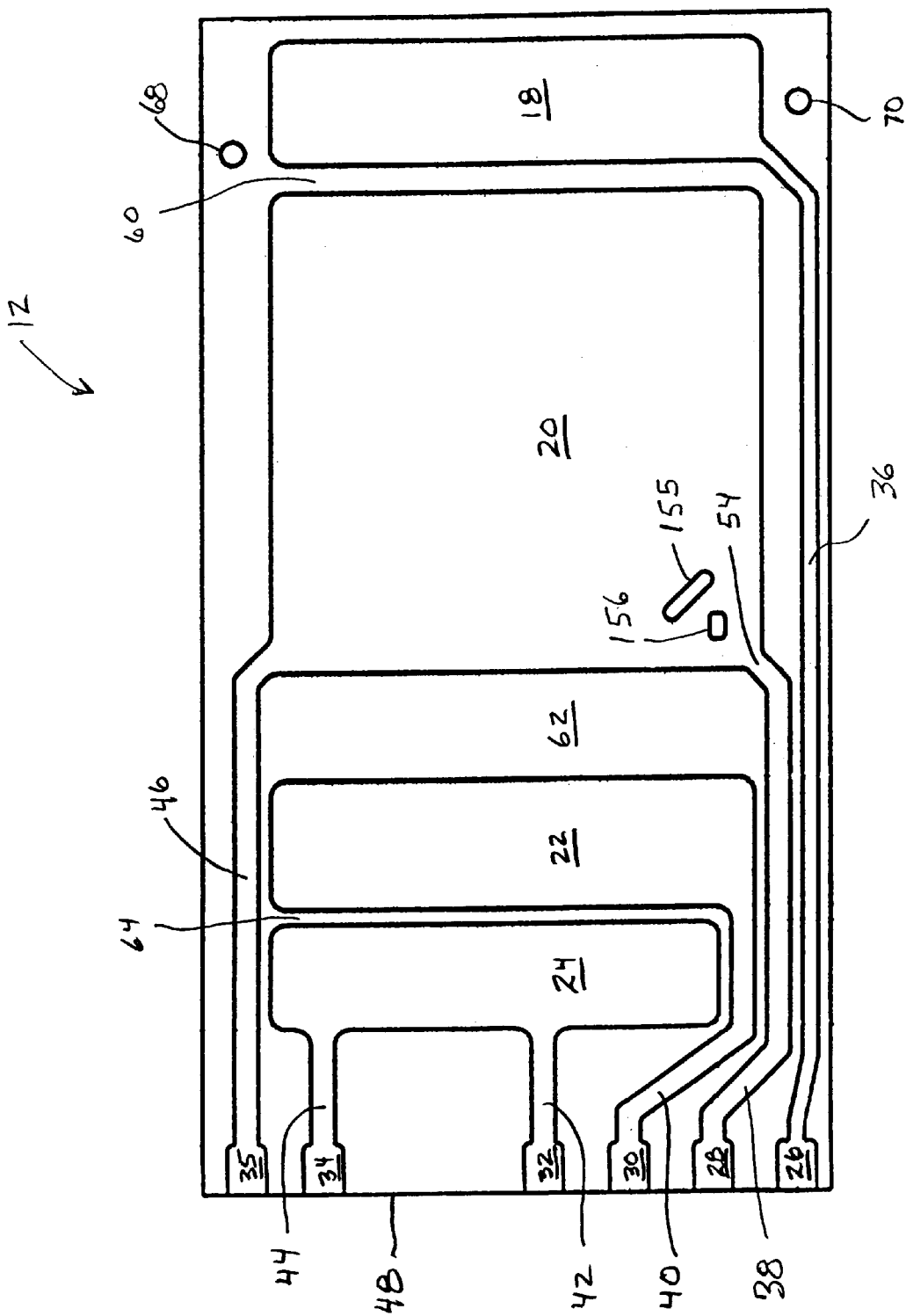
FIG. 5 is a plan view of a multi-chamber bag of the medication delivery container of FIG. 1, showing an alternate embodiment of the chamber flex absorbing pattern.
Figure 6:
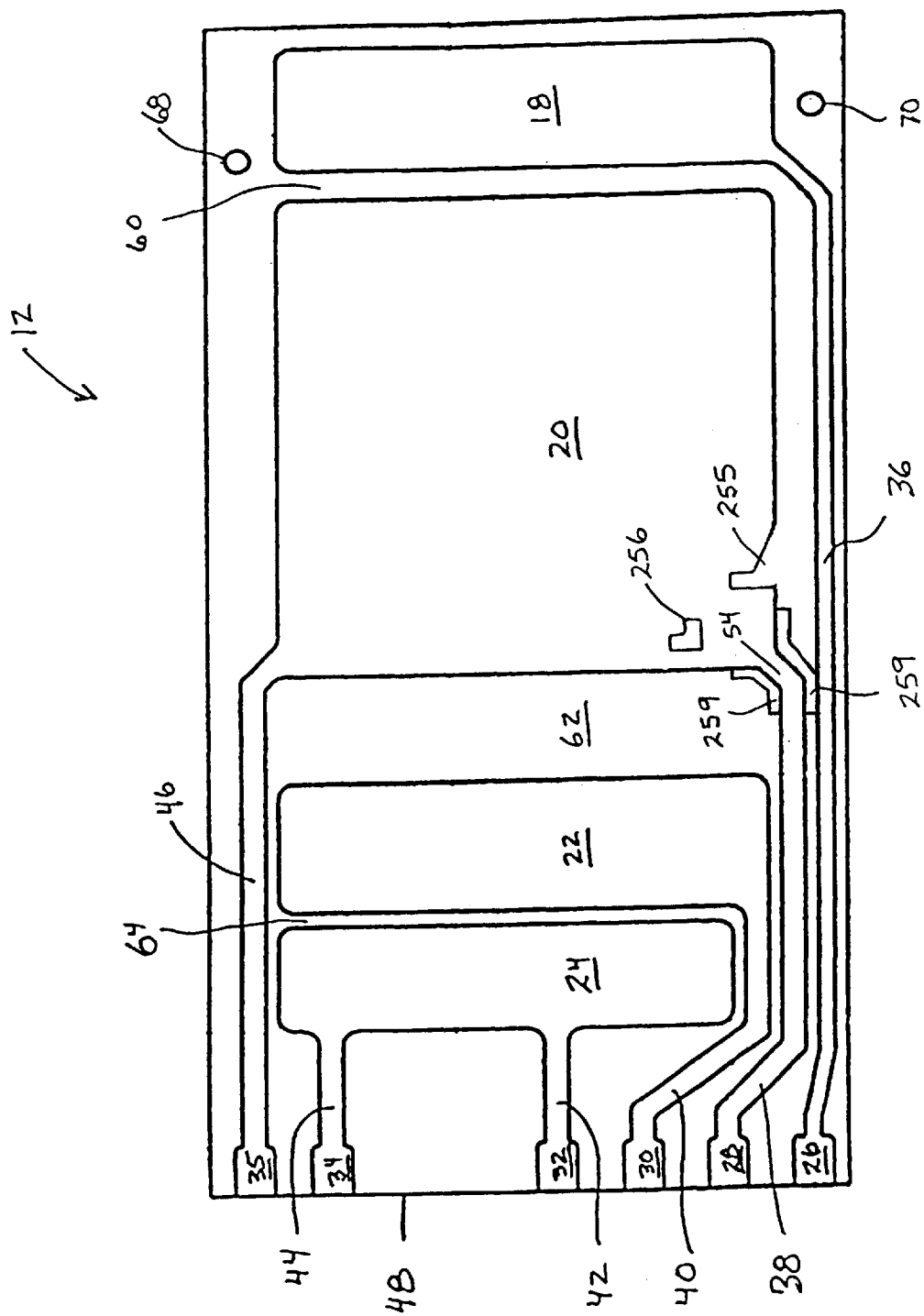
FIG. 6 is a plan view of a multi-chamber bag of the medication delivery container of FIG. 1, showing yet another embodiment of the e chamber flex absorbing pattern.
Figure 8:
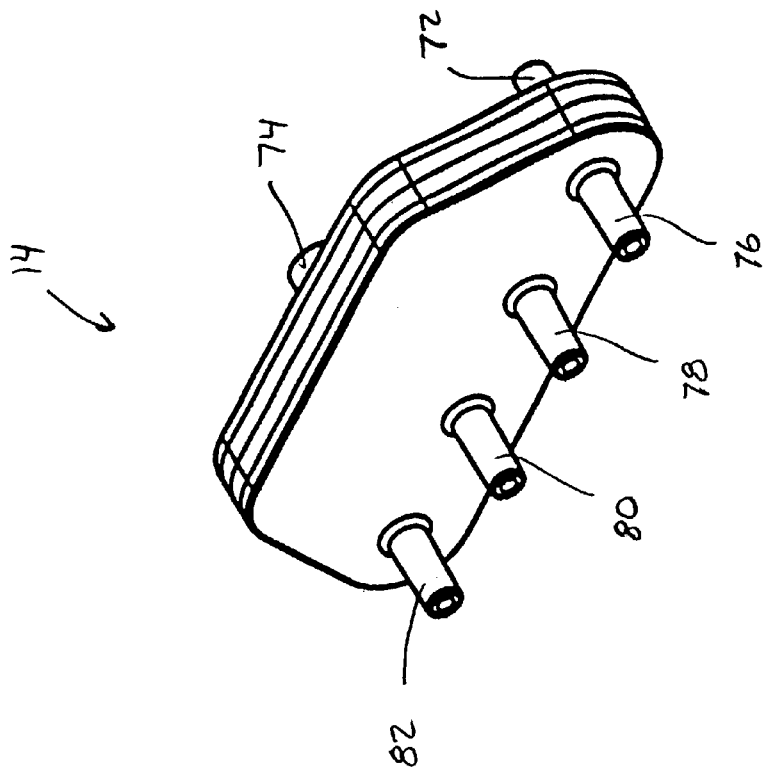
FIG. 8 is a perspective view of the manifold assembly of FIG. 7 from a reverse direction.
Figure 7:
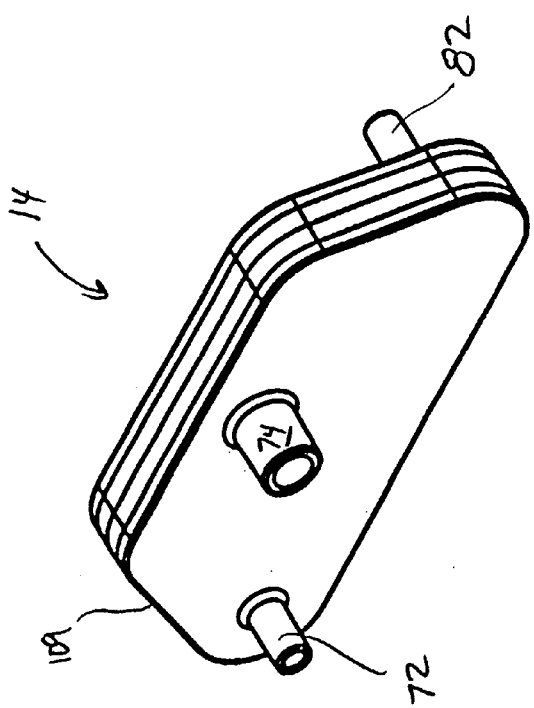
FIG. 7 is a perspective view of a manifold assembly of the medication delivery container of FIG. 1.

As used herein, "quilting" means forming a structure in the interior of the chamber wherein the bottom and top sides of the bag are connected, preferably by fusing them together. It is presently preferred that quilting be employed to manage pressure drop, as the desired connection between first and second sides of the bag can be accomplished by the same methods used to form the perimeter seal of the container. Quilting may be at any region of the chamber that provides a substantially reduced or eliminated pressure drop between the chamber and its corresponding conduit. It is presently preferred that the quilting be in the region of the chamber that is proximal to the conduit. In this region of the chamber, any one of a number of quilt shapes may be employed, including a T dot configuration, 55 and 56, as shown in FIG. 2, a dash dot configuration, 155 and 156, as shown in FIG. 5, bond blocks 255 and 256, as shown in FIG. 6, or the like. These types of quilting are discussed in greater detail below in reference to specific embodiments.

Other features suitable for minimizing flow resistance (i.e., pressure drop) caused by kinks include thermoforming of the conduit, introduction of an internal conduit bead in the region where the conduit joins the chamber, coining, or the like. Thermoforming involves heating the bag materials in the region of the exit and associated conduit until the materials are softened slightly. Air pressure is applied to the chamber to open (or inflate) the exit and the conduit. The material is allowed to cool such that the exit and conduit retain a slightly circular opening or cross-section after the pressure is removed. For employing internal conduit bead (s), a portion of the bag adjacent the exit to the conduit is stamped with an offset bonding pattern or shim to provide a three-dimensional structure in the region of the exit. (See, e.g., structure 259, FIG. 6). This can be analogized to gluing two sheets of paper together at their perimeter and affixing a solid piece, like a bamboo skewer along the length of the seam between the two sheets. In this manner, even when the two sheets are pressed together, a channel will exist along the skewer where the sheets are prevented from meeting one another. Additionally, coining (i.e., forming a structured pattern in the bag material) may be applied to the sides of the bag in the region of the exit to provide additional flow pathways not subject to greatly restricted flow by kinks.

It is contemplated that each conduit will have an associated port where, at a minimum, fluids exit the container. These conduits may serve the dual purpose of providing a channel for both the introduction of fluids into the chamber (s) and exit of fluids from the chambers. The container may have one or more ports for introduction of fluids into one or more of the individual chambers of the container. In one embodiment, these ports have associated conduits, separate from the exit conduits. The ports are configured to allow regulated, sterile introduction of fluids. This can be accomplished by fitting the ports with injection ports, or the like.

Because the container is to be subject to the sequential application of pressure, it is desirable for the container to be anchored inside the pump apparatus in a manner that prevents the pressure application device from merely moving the container ahead of it as the pressure is applied from one end of the bag to the other. Accordingly, it is presently preferred that the container be anchorable to the pump apparatus. This can be accomplished in a variety of ways, including the use of fasteners secured to the bag that will mate with counterpart fasteners in the pump apparatus. Such fasteners include hook and loop fasteners, snaps, buttons, zippers, and the like. In a presently preferred embodiment, the container is anchored by forming holes in a non-fluid containing portion of the bag, and mating these holes with corresponding protrusions such as pins, or the like, in the pump housing. These anchoring structures can serve the dual purpose of securing the bag and positioning it properly in the pump apparatus. This latter purpose can be accomplished by orienting the attachment structures so that there is only one orientation with which the bag can be positioned in the pump apparatus.

In another embodiment of the present invention, containers further comprise a manifold to regulate delivery of the medication from the bag port of the conduits to an administration tube set ("administration set"), and also optionally provides a structure for filling the container. As used herein, "bag port of the conduit" and "bag port" refer to the terminal portion of each conduit leading to/from a chamber in the bag. The bag ports may have an adapter affixed thereto for mating the bag ports with the manifold, or the manifold may be attached directly to the bag ports. The manifold can be any structure that is attachable to the bag ports (or adapters) in a fluid-tight manner while providing a common outlet for all bag ports to the administration set.

In describing the manifold, reference will be made to the bag side, where the manifold attaches to the bag ports, and the infusion side, where the manifold attaches to the administration set. Further reference will be made to chamber ports of the manifold, where the manifold attaches to and is in fluid communication with the bag ports. Accordingly, the chamber ports are on the bag side of the manifold. Additional reference will be made to an output port of the manifold, where the manifold attaches to and is fluid communication with the administration set. Although optional, it is presently preferred that the manifold also have a bulk fill port, where the manifold can be attached to, and be in fluid communication with, a source of fluid medications for introduction into the bag.

Manifolds contemplated for use in the practice of the present invention will have manifold conduits for directing fluid from chamber ports to the output port for exit to the administration set, and from the bulk fill port, when employed, to the chamber ports. These manifold conduits can be isolated from one another in a fluid-tight manner and can comprise internally molded chambers connecting the desired portions of the manifold, or they may comprise internally mounted tubing connecting the appropriate portions of the manifold, combinations thereof, or the like.

In order to regulate the flow of fluid through the manifold and to prevent backflow from the output port to the chamber ports, it is presently preferred that the manifold have check valves therein. Check valves can be configured in a variety of manners to regulate fluid flow as desired; all such configurations are contemplated as being within the scope of the present invention. In one embodiment of the present invention, fluid flow is regulated so that fluid exiting the container and entering the manifold through the chamber ports can only exit the manifold through the output port without returning to the bag by way of any other chamber port. This is accomplished by interposing a first check valve in a first conduit between each chamber port and the output port. The check valve only allows fluid to flow from the bag side of the manifold towards the infusion side where the output port is located.

It is important to note that some or all of the bag chambers may be individually filled by way of optional separate fill ports on the bag rather than by way of the optional bulk fill port of the manifold. In an embodiment of the present invention, when a bulk fill port is to be used, fluid flow in the manifold is further regulated so that fluid introduced through the bulk fill port can access one or more of the chamber ports for filling of chambers in the bag. Accordingly, chamber ports to be used for both filling and dispensing fluids will have two manifold conduits associated therewith: a first manifold conduit, as described above, for directing fluids from the chamber port(s) to the output port; and a second manifold conduit branching off of the first at a point between each chamber port and the first check valve. In this embodiment, a second check valve is located on each second manifold conduit between the chamber port and the bulk fill port. The second check valve only allows fluid to flow from the bulk fill port towards the chamber port. A schematic of one example of this embodiment is provided in FIG. 10, as further described below.

Any type of check valve can be employed in the practice of the present invention, including ball check valves, umbrella check valves, and the like. In a presently preferred embodiment of the present invention, an umbrella check valve is employed. Umbrella valves are inexpensive, simple in their operation and easy to install. Because umbrella valves are held in place by friction, it is presently preferred that the interior of the manifold be configured so that, upon assembly of the manifold, the umbrella valves are held securely in place by the internal structure of the manifold. This can be accomplished simply by having a structure that contacts the center of the umbrella portion (i.e., the dome of the umbrella) to bias the valve towards its associated passageway. In this manner, the force of liquid flowing past the valve will open but not unseat the valve.

The ports, valves and conduits of the manifold may be configured in any manner that permits the desired flow of fluid through the manifold. It is presently preferred that the conduits and output port be configured so that fluid exiting each sequentially activated bag chamber flows through its associated first check valve and then past all conduits leading from previously emptied bag chambers, before the output port is encountered. In this manner, residual fluid output from each bag chamber is pushed through the manifold and out through the output port by fluid from subsequently emptied bag chambers.

In order for the fluid flow to be further regulated (e.g., to prevent unintentional fluid flow from the bag through to the output port), it is desirable that the check valves be controllable as to when flow is permitted therethrough. This can be accomplished in a number of ways, depending on the type of check valve employed. For example, a valve can be employed having a threshold operating pressure (i.e., a cracking pressure) that opens the valve. The cracking pressure of the valve may be any pressure suitable for the intended application. Suitable cracking pressures should be no higher, obviously, than the pressure generated by the pump apparatus, yet high enough to prevent unintentional flow through the manifold. Cracking pressures can be in the range of about 0.25 lbs per square inch up to about 2 lbs per square inch. It is presently preferred that the cracking pressures be in the range of about 0.50 lbs per square inch up to about 1 lbs per square inch. In a most preferred embodiment, the cracking pressure is about 0.75 lbs per square inch. The cracking pressures should be consistent in a given direction of fluid flow. Thus, the check valves associated with the chamber ports and the output port can have one cracking pressure while the check valve(s) associated with the bulk fill port has a different cracking pressure. Due to economies of scale, it presently preferred that the valve types and cracking pressures be consistent throughout the manifold.

An administration set is optionally provided in one embodiment of the present invention. The administration set comprises a length of medical grade tubing, such as a micro-bore tube, or the like, with structures at each end: at one end (proximal end) for connecting the tubing to the output port of the manifold and at the opposite (distal) end for connection to a standard intravenous-type needle. Standard luer connectors, or the like may be used in the practice of the present invention.

The administration set may be further configured to regulate the rate of fluid administration to the patient. It is necessary to know the pressure generated by the pump/manifold combination in order to calibrate the delivery rate of the administration set. The pump apparatus generates predictable fluid pressures based on the volume of solution in each chamber. Using the predictable fluid pressures, the flow rate from the bag may be selectable using administration sets having predetermined tubing lengths and inner diameters. The flow rate through the administration set is selected by varying the microbore tubing's inner diameter and length. The relationship is approximated by Poiseulle's equation:

$$Q = \frac{\Delta p \cdot \pi \cdot D^4}{128 \cdot \mu \cdot L} \qquad \text{Equation 1}$$

Where Q is the flow rate, $\Delta p$ is the pressure drop across a flow controlling orifice, D is the inside diameter of the orifice, $\mu$ is the dynamic viscosity of the fluid and L is the length of the orifice. Thus, any structures included in the administration set will effect the flow rate in a predictable and calculable manner. Structures contemplated for optional incorporation into the administration set include particulate filters, air elimination filters, fluid flow restrictors, and the like. The administration set may further comprise a clamp, or the like, for stopping fluid flow, as desired.

In another embodiment of the present invention there is provided a restrictor set for attachment to the distal end of the administration set. In this manner, the rate of fluid flow can be altered with the simple addition of a restrictor set, rather than by re-engineering the administration set. Of course, the maximum fluid flow rate will be determined by the configuration of the administration set, with fine-tuning to slower rates provided by the restrictor set.

The invention will now be described in greater detail by reference to specific, non-limiting embodiments. Moreover, each of the embodiments of the various components described below need not necessarily be used in conjunction with the other specific embodiments shown.

With reference to FIGS. 1 and 2, the medication delivery container 10 of the invention includes a multi-chamber bag 12, a manifold assembly 14 and a tube assembly 16. The container provides improved infusion therapy administration which is particularly advantageous for reducing errors, infections and other complications associated with manual infusion techniques.

Figure 3:
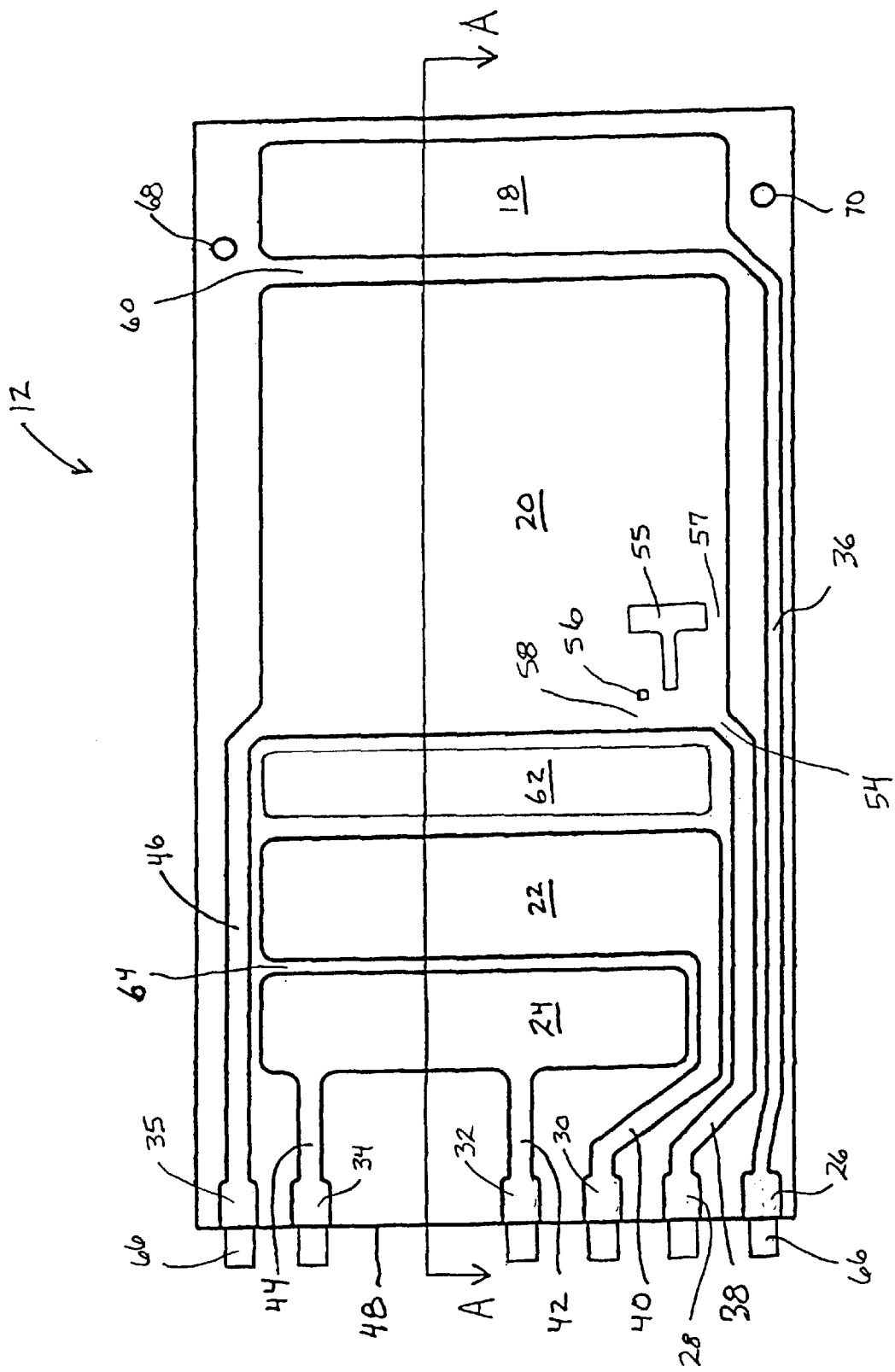
FIG. 3 is a plan view of a multi-chamber bag of the medication delivery container of FIG. 1, showing the bag's chambers and conduits and one embodiment of a chamber flex absorbing pattern.
Figure 4:
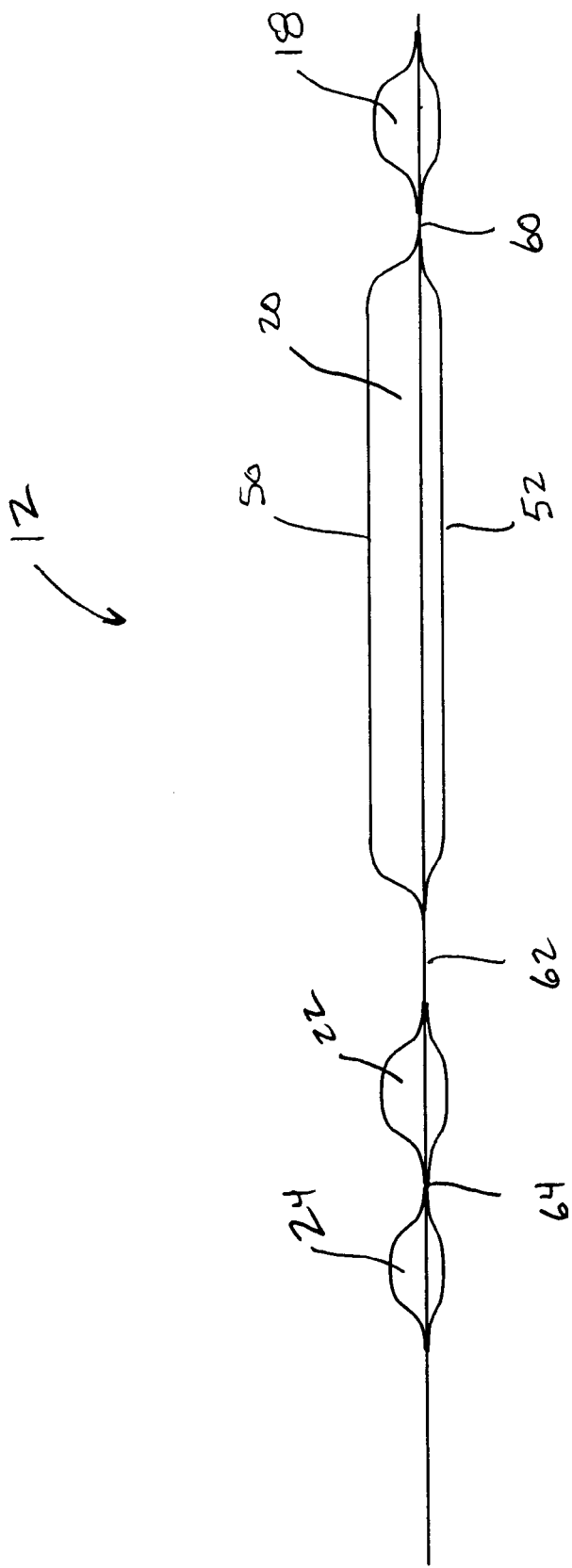
FIG. 4 is a cross-sectional view along line A—A of a multi-chamber bag of FIG. 3.

The multi-chamber bag, as shown in FIGS. 3 and 4, may include four chambers 18, 20, 22 and 24, six ports 26, 28, 30, 32, 34 and 35, and six conduits 36, 38, 40, 42, 44 and 46 for coupling each of the respective ports to a chamber. The multi-chamber bag may have other chamber, port and conduit configurations of varying number, sizes, and shapes in accordance with the invention. The ports may lie at the end 48 or along one or more edges of the bag. The chambers comprise a relatively large area of the bag in a central portion of the bag and are configured to be filled with medication fluids or pharmacological agents. The central chamber portion of the bag may be referred to as a compression region which is sequentially compressed by application of an external force to drive liquid from the chambers through the respective conduits and out the ports in accordance with the infusion therapy. The conduits generally lie outside of the compression region to avoid residual medications in the conduits from mixing with subsequently administered medications from other chambers. The conduits may lie within the compression region particularly if mixing is not a concern.

The multi-chamber bag 12 is formed of two flexible sheets 50 and 52, of material and has a generally rectangular flat shape. The flexible sheets may be ethyl vinyl acetate (EVA), polyvinyl chloride (PVC), polyolefin or other suitable material. One sheet may have a relatively smooth inner surface and the other sheet may have a taffeta texture (or similar pattern that is not smooth, such as ribs) embossed on its inner surface. Alternatively, both sheets may have an inner surface that is not smooth. The sheets are bonded together to create the patterns for the chambers, conduits, and ports. The materials may be bonded by suitable means, e.g., by a radio frequency (rf) seal, sonication, by heat seal, adhesive, or the like, to form an air and fluid tight seal between the chambers and the conduits. When filled with medication fluids, the chambers bulge creating a "pillow-like" shape (FIG. 4).

The first chamber 18 is furthest from the port side 48 of the bag and may contain a first medication fluid of an infusion therapy sequence. The first chamber is coupled to a first bag port 26 by a first conduit 36. The first chamber is filled with fluid through the first bag port.

The spacings 60, 62 and 64 between the chambers advantageously provides a "blow-down" period during an infusion sequence to prevent mixing of medications during the infusion. The spacing 62 between the second chamber 20 and the third chamber 22 is sized based on the time needed for the chamber and conduit to "blow down", or flow until the residual pressure is below the cracking pressure of the associated check valves in the manifold. The area of the spacing 62 may be sealed only around the perimeter with no bond between the sheets in the central spacing area to provide additional kink and flex absorbing characteristics to the bag. This spacing 62 is configured to allow a sufficient time period between the infusion of the medication in the second chamber and the beginning of the infusion of medication in the third chamber so as to minimize or prevent mixing of the medication in the second chamber with the medication in the third chamber. This time period is sufficient to allow the material spring strength of the flexible sheets, 50 and 52, that form the conduits to pull the respective conduit 38 flat to expel residual fluid from the conduit. The time required will, of course, vary with the size of the chamber, the rate of infusion, and the like. Note that the spacing 60 between the first chamber 18 and the second chamber is effectively as large as the spacing 62 because a significant portion of the second chamber must be compressed before the pressure is sufficient to expel residual fluid from the second chamber. Thus, the spacing between chambers provides a delay between chambers to allow expulsion of residual conduit fluid before the start of the infusion of medication from the next chamber. This is especially advantageous for preventing mixing of agents from non-adjacent chambers.

The second chamber 20 typically has the largest fluid volume of the four chambers. As discussed in more detail below, the second chamber is coupled to the second port 28 and the sixth port 35 by respective conduits. When filled with medication, the second chamber has a pillow-like shape. As a result of the relatively large pillow-like shape of the second chamber (and the flexible nature of the materials used to construct the bag), when pressure is applied to the second chamber, there may be a resistance to flow because the chamber has a tendency to kink near the chamber exit 54 to the conduit, often cutting off fluid flow to the conduit. To prevent a pressure drop due to kinks from forming at the exit port, a "quilt" pattern of bonds may be placed near the exit. The quilt pattern may consist of two spot bonds, 55 and 56, having a "T dot" configuration. The quilt pattern moves the chamber's kinking tendencies to other areas of the bag where kinking is not of concern, away from the exit 54. The first bond 55 has a "T" shape providing first and second openings, 57 and 58. From observation, it appears that the cross bar of the T causes the chamber to kink laterally and preferentially above the outlet 54. The leg of the T further causes a longitudinal kink away from the outlet 54. After the chamber has been compressed to the first opening 57, the "pillow" of the compressed chamber is of a size that is less susceptible to exit kinks. The second "dot" bond further discourages kinking of the second opening 58. The quilt pattern may be provided to other ports of the chamber to prevent kinking while removing air, etc. Empirical tests have determined that the quilt pattern configuration discourages kinks at the exit and allows reliable delivery of the medication from the second chamber into the respective conduit 38.

In an alternative embodiment of the invention, the quilt pattern may consist of the two spot bonds, 155 and 156, shown in FIG. 5. The first spot bond 155 may have a generally elongated oval shape and may be preferably placed at a 45 degree angle with respect to the chamber sides. The second spot bond 156 may have a shorter oval shape and is preferably placed between the first spot bond and the exit or entrance to conduit 38.

In another embodiment of the invention, the quilt pattern may consist of the bond blocks, 255 and 256, shown in FIG. 6. The first bond block may have a generally elongated angle shape with a protrusion and may be preferably placed about ½ inch from the exit 54 to conduit 38. The second bond block may have a corner shape and is preferably placed nearly between the first bond block and the exit 54 (or entrance) to conduit 38.

Referring to FIG. 2, the third chamber 22 is coupled to the third port 30 by a respective conduit 40. The fourth chamber 24 is coupled to the fourth and fifth ports, 32 and 34, by respective conduits 42 and 44.

The six ports are used to fill and/or empty the fluid in the chambers. Two of the ports, the fifth and sixth ports, 34 and 35 (see FIG. 2, for example), are directly coupled to the fourth chamber 24 and second chamber 20, respectively. The four remaining ports, 26, 28, 30 and 32, are coupled to a manifold assembly 14 for filling the chambers and for delivering the medications of the infusion therapy. A short plastic tube 66 couples each respective port to the respective manifold port or injection fill site 67. The tubes extend into the ports between the plastic sheets, 50 and 52, and are sealed to the sheets to form closed, sealed fluid connections. The tubes may be formed of co-extruded plastic for providing a compatible bonding surface. For example, if the bag 12 is formed of EVA and the manifold is formed of acrylonitrile butadiene styrene (ABS), the co-extruded tube 66 would have an exterior of EVA and an interior of PVC. The outside of the tube EVA would be heat sealed to the bag (EVA) and the inside of the tube (PVC) would be solvent bonded to the outside of a corresponding port of the manifold (ABS).

In one application of the invention, the first, second and third chambers, 18, 20 and 22, may be filled with a diluent such as a saline solution, a dextrose solution or sterile water, and the fourth chamber 24 is filled with heparinized saline. A medication, such as an antibiotic, may be injected into the second chamber through the sixth port 35 before commencing delivery of the infusion therapy to a patient. Also, the fourth chamber may be filled through the fifth port 34 before commencing delivery of the therapy.

The multi-chamber bag 12 also may include a plurality of alignment holes, e.g., 68 and 70. The alignment holes may be offset and aligned with corresponding features such as pins in a pump. The alignment holes ensure that the bag is installed into the pump in the correct position, and maintained in that position during pumping.

Figure 9:
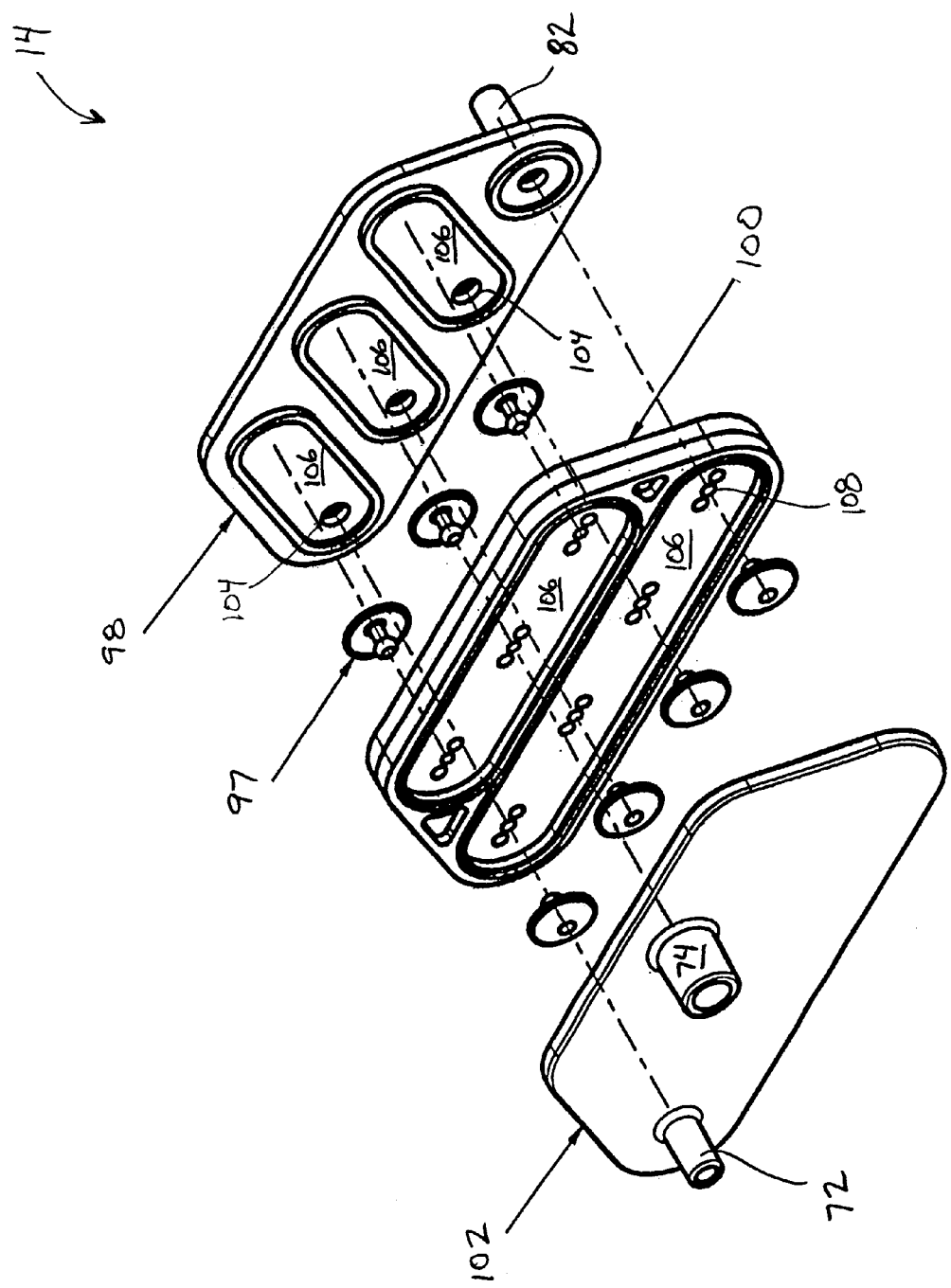
FIG. 9 is an exploded perspective view of the manifold assembly of FIG. 7.
Figure 10:
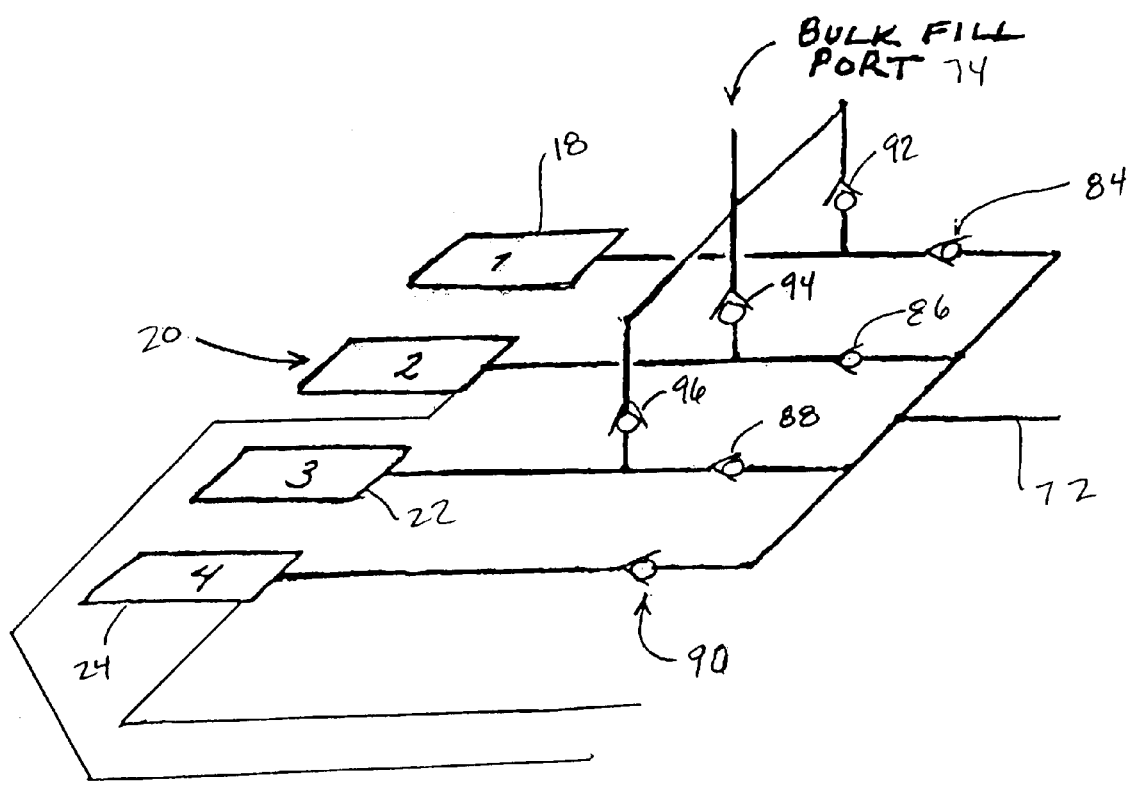
FIG. 10 is a schematic diagram showing the internal conduit and valve configuration of the manifold assembly of FIGS. 7–9.

With reference to FIGS. 7–10, the manifold assembly 14 has a tube or output port 72, a bulk fill port 74 and four chamber ports 76, 78, 80 and 82. The four chamber ports are connected, respectively, to the first, second, third and fourth bag ports 26, 28, 30 and 32. The manifold assembly allows filling of the first, second and third chambers, 18, 20 and 22, through the bulk fill port and delivery of the fluids in the first, second, third and fourth chambers through an output port. Seven check valves, 84, 86, 88, 90, 92, 94 and 96, control the fluid flow direction within the manifold, in concert with manifold conduits formed by bonding manifold pieces together (FIG. 10). The manifold assembly may have additional or fewer check valves and ports based on the number and configuration of chambers implemented by the multi-chamber bag.

In a particular embodiment, as shown in FIG. 9, for example, the manifold assembly may be constructed of three molded pieces and seven check valves. The three molded pieces may be formed of any suitable biologically compatible rigid or semi-rigid material, e.g., ABS plastic, or the like. The three molded pieces are a bag side piece 98, a middle piece 100, and an infusion side piece 102. The bag side piece has the four chamber ports 76, 78, 80 and 82. The bag side piece also has recesses 104 for three of the umbrella valves 97 and conduits 106 for directing fluid flow between the ports in conjunction with the other manifold pieces. The middle piece 100 has valve through holes 108 for receiving the umbrella valves and for providing fluid communication through the middle piece. The middle piece also has conduits on both sides that correspond to the conduits on the respective side pieces. The infusion side piece 102 includes the output port 72 and the bulk fill port 74. The infusion side piece also has internal recesses (not shown) for four of the umbrella valves and conduits (not shown) for directing fluid flow within the manifold assembly, as well as protrusions designed to contact the middle of the dome of the umbrella for biasing the check valve in the proper position. The three manifold pieces are attached together by suitable adhesive, clips or the like to form the manifold assembly. The manifold assembly can be further shaped so that it can only be correctly placed in a corresponding receptacle in the pump apparatus. For example, the manifold may include one or more beveled edges 109 (FIG. 7) for correctly aligning the container 10 in a pump mechanism.

The outlet port 72 of the manifold assembly is connected to the administration set 16. The administration set may include a micro-bore tube 110 having a length and diameter selected to restrict the fluid flow through the tube assembly to a predetermined delivery rate. The tube also may include an air-eliminating filter 112 that eliminates during infusion any air that may get into the apparatus of the medication delivery container. At the end of the tube set is a luer connector 114 that couples the tubing assembly to the patient injection site. The administration set may also include a clamp 116 after the air-eliminating filter. The tube may be primed by filling the manifold assembly and the tube through the bulk fill port while the clamp is locked until the air is eliminated through the air-eliminating filter. Further, a hydraulic lock may be formed between the air-eliminating filter and the valves by filling the manifold assembly and the tube to a sufficient positive pressure to prevent the valves from opening and allowing leakage from the chambers during storage, handling, or transport.

The medication delivery container 10 may have a wide variety of configurations and dimensions based on the prescribed infusion therapy. For example, when infusion therapies permit (e.g., when small volumes of concentrated solution are to be infused), bags may be sufficiently small to incorporate into an easily portable pump apparatus. Chambers may be configured for the simultaneous infusion of medicaments from separate chambers. Empirical evaluation of the container and manifold configuration shown in FIGS. 1–10 has demonstrated effective delivery of fluids.

The entire disclosures of U.S. application Ser. No. 09/008, 111 and application Ser. No. 09/235,535, both titled "Medication Delivery Apparatus", and of U.S. applications titled "Medication Delivery Pump" (further identified by attorney docket number TAND1140), and "Medication Delivery System" (further identified by attorney docket number TAND1150), both filed concurrently on the same date as this application, are incorporated herein by reference.

While the invention has been described in detail with reference to certain preferred embodiments thereof, it will be understood that modifications and variations are within the spirit and scope of that which is described and claimed.

What is claimed is:

1. A medication delivery container, comprising:
   a bag comprising a plurality of chambers; and
   a plurality of bag ports through an outer surface of said bag, each said chamber in fluid communication with at least one said bag port and;
   a manifold assembly comprising a plurality of manifold ports integrally coupled to said bag ports, and at least one common port, whereby each said chamber is in fluid communication with at least one said manifold port to provide a flow path for delivering medications out of said chambers to said common port.

2. A medication delivery container according to claim 1, further comprising an administration set coupled to at least one common port of the manifold assembly for delivering medications from the manifold assembly to an infusion site.

3. A medication delivery container according to claim 2, wherein said administration set comprises one or more of an air elimination filter, a particulate filter, and a restrictor set.

4. A medication delivery container according to claim 1, wherein one or more of conduits provide fluid communication between one or more chambers and or more bag ports.

5. A medication delivery container according to claim 4, wherein the plurality of chambers lie within a compression region of the bag and the plurality of conduits generally lie outside of the compression region of the bag.

6. A medication delivery container according to claim 4, wherein the bag is formed of two flexible sheets of plastic bonded together in a pattern that forms the plurality of chambers and the plurality of conduits.

7. A medication delivery container according to claim 6, wherein one sheet of plastic has a relatively smooth surface and the second sheet of plastic has a textured surface, wherein flexible sheets are bonded such that the smooth surface faces the textured surface to form flow channels between the sheets at locations associated with the chambers and the conduits.

8. A medication delivery container according to claim 6, wherein each sheet of plastic has a textured surface, wherein flexible sheets are bonded such that the textured surfaces are adjacent to form flow channels between the sheets at locations associated with the chambers and the conduits.

9. A medication delivery container according to claim 1, further comprising a plurality of exit ports between the respective plurality of chambers and plurality of conduits, wherein at least one chamber has a bond adjacent to the exit port to discourage the exit from closing upon the application of pressure to said chamber.

10. A medication delivery container according to claim 1, further comprising a plurality of exit ports between the respective plurality of chambers and plurality of conduits, wherein at least one chamber has a quilt pattern of bonds adjacent to the exit port to discourage the exit from closing upon the application of pressure to said chamber.

11. A medication delivery container according to claim 10, wherein the quilt pattern of bonds has a T-dot configuration.

12. A medication delivery container according to claim 1, further comprising a structure for alleviating pressure drop, said structure being associated with at least one chamber to allow fluid flow from the respective chamber to an associated conduit upon the application of pressure to the respective chamber.

13. A medication delivery container according to claim 12, wherein the structure for alleviating pressure drops comprises a thermoformed conduit having a normally open shape.

14. A medication delivery container according to claim 12, wherein the structure for alleviating pressure drops comprises internal conduit beads adjacent to an intersection between the respective chamber and the associated conduit.

15. A medication delivery container according to claim 12, wherein the structure for alleviating pressure drops comprises a quilt pattern of bonds adjacent to the exit port to discourage the exit from closing upon the application of pressure to said chamber.

16. A medication delivery container according to claim 1, wherein the bag is formed of two flexible sheets of EVA plastic, the manifold is formed of ABS plastic, and the bag further comprises a plurality of ports, each port associated with a chamber of the bag, a plurality of co-extruded tubes, each tube having an exterior surface of EVA plastic that is heat seal bonded to the plastic sheets at the respective port and an interior surface of polyvinylchloride (PVC) that is solvent bonded to a corresponding port of the manifold.

17. A medication delivery container according to claim 1, further comprising a spacing between at least two selected adjacent chambers that is configured to allow a time period between the delivery of fluid from the selected adjacent chambers to reduce mixing of the respective chamber fluids.

18. A medication delivery container according to claim 1, wherein the manifold assembly includes a bulk fill port for filling a plurality of the bag's chambers.

19. A medication delivery container according to claim 2, wherein the administration set includes a micro-bore tube for controlling the fluid flow rate from the bag.

20. A medication delivery container according to claim 3, wherein the manifold assembly includes a plurality of back check valves, each back check valve associated with a respective chamber of the bag, and wherein a hydraulic lock may be formed between the back check valves and the air-eliminating filter to prevent leakage of fluid from the chambers during storage, handling, or transport of the container.

21. A fluid delivery container, comprising:
    a bag having at least one flexible fluid chamber; and exit port within a wall of the chamber, and a conduit in fluid communication with the chamber via the exit port and one or more structures for minimizing pressure drop between the chamber and the conduit by inhibiting restriction of fluid flow through the exit port upon the application of pressure to the chamber.

22. A fluid delivery container according to claim 21, wherein the structure for minimizing pressure drop comprises a bond adjacent to an exit port of the chamber to discourage the exit port or associated conduit from closing upon the application of pressure to said chamber.

23. A fluid delivery container according to claim 21, wherein the structure for minimizing pressure drop comprises a quilt pattern of bonds adjacent to an exit port of the chamber to discourage the exit port or associated conduit from closing upon the application of pressure to said chamber.

24. A fluid delivery container according to claim 23, wherein the quilt pattern of bonds has a T-dot configuration.

25. A fluid delivery container according to claim 21, wherein the structure for minimizing pressure drop comprises internal conduit bead(s) between the plastic sheets in a region of the container where the chamber and its associated conduit meet.

26. A fluid delivery container according to claim 21, wherein the structure for minimizing pressure drop comprises thermoformed conduit having a normally open shape.

27. A medication delivery container according to claim 1, wherein said manifold assembly further comprises a fill port and a flow path for delivering fluids from said fill port into one or more chambers.

28. A medication delivery container, comprising:
    a bag comprising a plurality of chambers;
    a manifold assembly coupled to the plurality of chambers for delivering medications out of the chambers; and
    a plurality of exit ports for egress of fluid from said chambers, wherein at least one chamber has a quilt pattern of bonds adjacent to its corresponding exit port to discourage said corresponding exit port from closing upon the application of pressure to said chamber.

29. A medication delivery container according to claim 28, wherein the quilt pattern of bonds has a T-dot configuration.

30. A medication delivery container, comprising:
    a bag having at least one fluid chamber; and
    structure for minimizing pressure drop between the chamber and an associated conduit upon the application of pressure to the chamber, wherein the structure for minimizing pressure drop comprises a quilt pattern of bonds adjacent to an exit port of the chamber to discourage the exit port or associated conduit from closing upon the application of pressure to said chamber.

31. A medication delivery container according to claim 30, wherein the quilt pattern of bonds has a T-dot configuration.

32. A medication delivery container, comprising:
    (a) a bag comprising
        (i) a plurality of chambers,
        (ii) a plurality of bag ports through an outer surface of said bag, wherein each said chamber is in fluid communication with at least one said bag port via a conduit, and
        (iii) a plurality of exit ports connecting each said chamber to an associated conduit,
    wherein said bag is configured and arranged such that each chamber does not overlap with any adjacent chamber along at least one axis of said bag, and said bag ports are positioned substantially perpendicular to said axis along an edge of said bag; and
    (b) a manifold assembly comprising a plurality of manifold ports and at least one common port, wherein each said chamber is in fluid communication with at least one said manifold port,
    whereby fluid flow within said medication delivery container occurs from each said chamber via an associated exit port, an associated conduit, an associated bag port, and an associated manifold port, to said common port.

33. A medication delivery container according to claim 32, wherein at least one chamber has a quilt pattern of bonds adjacent to an associated exit port to discourage the exit port from closing upon the application of pressure to said chamber.

34. A medication delivery container according to claim 33, wherein the quilt pattern of bonds has a T-dot configuration.

* * * * *

UNITED STATES PATENT AND TRADEMARK OFFICE
CERTIFICATE OF CORRECTION

PATENT NO.    : 6,428,518 B1
DATED         : August 6, 2002
INVENTOR(S)   : David R. Brengle et al.

It is certified that error appears in the above-identified patent and that said Letters Patent is hereby corrected as shown below:

Column 11,
Line 54, after "port" insert a semi-colon
Line 54, after "and" delete the semi-colon Column 12,
Line 2, after "more" delete "of"
Line 3, after "and" insert -- one --

Column 13,
Line 19, after "chamber" delete the semi-colon and insert a comma
Line 19, after "chamber," change the word "and" to -- an --
Line 21, after "port" insert a semi-colon Signed and Sealed this Twenty-first Day of January, 2003

JAMES E. ROGAN
*Director of the United States Patent and Trademark Office*